United States Patent [19]

Cabane et al.

[11] 4,416,987
[45] Nov. 22, 1983

[54] METHOD OF SYNTHESIZING PROTEINS FROM METHANOL

[75] Inventors: Bruno Cabane, Saint Cloud; Pierre Galzy, Montpellier, both of France

[73] Assignee: PCUK - Produits Chimiques Ugine Kuhlmann, Courbevoie, France

[21] Appl. No.: 322,566

[22] Filed: Nov. 18, 1981

Related U.S. Application Data

[63] Continuation of Ser. No. 859,873, Dec. 12, 1977, abandoned.

[30] Foreign Application Priority Data

Dec. 14, 1976 [FR] France ............................. 76 37604
May 27, 1977 [FR] France ............................. 77 16283

[51] Int. Cl.$^3$ ............................................. C12N 15/00
[52] U.S. Cl. ................................... 435/68; 435/172;
   435/247; 435/253; 435/804; 435/859; 435/874
[58] Field of Search ............... 435/172, 247, 253, 804,
   435/813, 859, 874, 68; 426/656

[56] References Cited

U.S. PATENT DOCUMENTS

| | | | |
|---|---|---|---|
| 2,571,115 | 10/1951 | Davis | 435/172 |
| 3,756,916 | 9/1973 | Leavitt | 435/253 |
| 4,060,455 | 11/1977 | Wagner et al. | 435/247 |
| 4,086,137 | 4/1978 | Nakayama et al. | 435/172 |

OTHER PUBLICATIONS

Clarke et al., *Genetics and Biochemistry of Pseudomonas*, John Wiley & Sons, London, (1975), pp. 134–139 & 232–240.

Ribbons et al., "Metabolism of Single Carbon Compounds", *Ann. Rev. Microbiol.*, vol. 24, (1970), pp. 146–151.

Whittenberg et al., "Enrichment & Isolation and Some Properties of Methane-Utilizing Bacteria", *J. Gen. Microbiol.*, vol. 61, (1970), pp. 205–218.

Shanthama et al., "Quantitative Assessment of the Mutagenic Effect of Ethyl Methane Sulfate in *Micrococcus glutomicus*", *Chem. Absts.*, vol. 77, No. 5, pp. 98, 99, (1972), Abst. No. 29590t.

Asthana et al., "Growth of Yeast on Methanol as the Sole Carbon Source", *Biotech. Bioeng.*, vol. XIII, (1971), pp. 923–929.

Hirsch et al., "Biology of Budding Bacteria", *Archiv. fur Mikrobiol.*, (1964), pp. 358–367.

Harder et al., "Methanol Assimilation by *Hyphomicrobium sp.*", *J. Gen. Microbiol.*, vol. 78, (1973), pp. 155–163.

Reuss et al., "Extended Culture of *Candida boidinic* on Methanol", *European J. App. Microbiol.*, vol. 1, (1975), pp. 295–305.

*Primary Examiner*—Esther M. Kepplinger
*Attorney, Agent, or Firm*—Pennie & Edmonds

[57] ABSTRACT

The invention disclosed provides a method for synthesizing proteins by means of strains of microorganisms improved as regards their performances in using methanol.

5 Claims, No Drawings

METHOD OF SYNTHESIZING PROTEINS FROM METHANOL

This is a continuation of application Ser. No. 859,873, filed Dec. 12, 1977, now abandoned.

BACKGROUND OF THE INVENTION

1. Field of the Invention

The present invention relates to a method of synthesizing new improved proteins from a methanol containing culture, by means of methylotrophic microorganisms selected as glycine resistant mutants.

2. Description of the Prior Art

Numerous attempts have been made in the prior art to prepare methylotrophic microorganisms using methanol by way of serine (2-amino-3-hydroxypropionic acid). Those microorganisms which have been isolated by the conventional methods such as repeated picking out of the microorganisms from a medium using methanol as the sole source of carbon, have kinetic performances which are frequently mediocre.

In methods of producing proteins from unicellular organisms, the strain of microorganisms is of considerable importance. For a given carbon substrate, the biological values of the product, such as absence of toxicity, the degree of nutritional value, or the like, depend upon the particular strain. Also, the economics of continuous industrial production of the proteins are highly dependent upon the particular strain so it is important that the selection be performed with certainty and care. A most important value of a particular strain would appear to be the kinetic performances of the strain which dictates the extent of the scale of the industrial installation and, hence, the capital investment required.

Although the methods of isolating strains by continuous selection make it possible to isolate the performing strains, these methods are, nevertheless, protracted since it takes at least one month of experimentation in a continuous fermenter. The methods are delicate and the results hazardous. On the other hand, only an enrichment of microorganism is achieved in this way and it is essential to isolate the best performing microorganism from the complex flora being processed.

Some of the prior art attempts are described in the literature, more particularly, in the following texts: W. Harder, M. M. Atwood, J. R. Quayle, J. Gen. Microbiol. (1973) 78 155-163, Asthana et Coll. Biotechnol, Bioeng. (1971) 13, 923 and (1971) 8, 923, M. Reuss et Coll. Eur. J. Appl. Microbiol. (1975) 1, 295-305, Whittenbury et al. J. Gen. Microbiol. (1970), 61 205, Hirsh and Conti Archiv. Fin Mikrobiologie (1964) 43; 358, Ogata et Coll. J. Ferment. Technol. (1970) 48, 470.

Applicants have discovered that, among the strains which metabolize methanol by way of serine, the resistance to glycine habitually involves an increased utilization of methanol.

It has now been found that, by practice of the present invention proteins may be prepared from methanol with improved strains which are characterized as glycine-resistant methylotrophic strains.

SUMMARY OF THE INVENTION

Generally stated, the present method provides a method for synthesizing proteins by culturing a strain of microorganisms in a methanol containing medium. The harvested cellulor suspension from the culture is diluted and then disposed in a glycine-containing culture from which glycine-resistant mutants are recovered. The glycine-resistant mutants are then cultured and recovered.

An object of the present invention is to synthesize proteins with strains of microorganisms which are characterized as glycine-resistant methylotrophic strains.

Another object of the present invention is to provide a method of improvement for methylotrophic strains, the strains being disposed in a glycine-containing culture from which may be recovered glycine-resistant mutants.

Other objects, advantages and features of the present invention will become more apparent from the following detailed description.

DESCRIPTION OF THE PREFERRED EMBODIMENTS

By practice of the present method, it is possible to use for the manufacture of proteins from methanol, an improved strain of any one of the strains exhibiting the characteristic of utilization of methanol by way of serine. The improvement of said methylotrophic strain consists, on the one hand, in an increase in the affinity for methanol and, on the other hand, in a reduction of the generation time on methanol carbon substrate.

The increase in affinity for methanol may be determined by its apparent constant affinity for methanol ($K_s$) determined in parts per million (ppm) which may be measured by gas phase chromatography.

Practice of the present method makes it possible to use improved strains of methylotrophic microorganisms using methanol metabolically known as serine. The improvement of the strains, making their kinetic performances compatible with a continuous method of industrial production of proteins from methanol, by means of the present invention can be applied to a large number of microorganisms such as, non-limitatively, microorganisms of the following types: Bacillus, Micrococcus, Arthrobacter, Flavobacterium, Pseudomonas, Aeromonas, Methylomonas, Rhodopseudomonas, Methylococcus, Klebsiella, Rhodospirillum, Rhodomicrobium, Hyphomicrobium, Acinetobacter, Achromobacter, Moraxella, and the like, by way of example.

The improved methylotrophic strains presently prepared are distinguished from the wild strains from which they issue, by their resistance to the effect of glycine.

The improved methylotrophic strains remain insensitive to the action of glycine for concentrations of amino acid at least ten times higher than those which cause a beginning in the inhibition of the use of the methanol substrate (increase in $K_s$) in the wild strain.

The improved methylotrophic strain, by practice of the present invention, can grow on a medium composed of methanol substrate and glycine, whereas the corresponding wild strain is incapable of growing in the presence of these concentrations of glycine. Desirably, the concentration of the glycine in the medium is about 0.5% to 2% by weight.

The method of the invention consists in selecting glycine-resistant mutants from optional methylotrophic strains, and the recovered mutants can then be cultured. The culture of the strain is found to possess improved characteristics in the following way:

The cells are harvested, preferably in the exponential stage of growth, then spread on a selection sieve comprising a solid medium for methylotrophic microorganisms, plus about 0.5% to 2% by weight glycine, either directly, or after the preliminary action of a physical or chemical mutagenic agent.

All the strains thus selected exhibit the character of resistance to glycine in concentrations from about 0.5% to 2%.

The improved strains are inoculated into a culture medium which contains mineral salts, nitrogen in mineral form and methanol in concentrations variable from 0.1 to 2% (weight/volume). The methanol, sterilized by filtration, is added to the autoclaved medium heated to 120° C. for 30 minutes. The pH should be adjusted between 6 and 8.

The culture is performed in sterile flasks, with sufficient agitation such that the aeration is not limiting, and at temperatures which may vary from about 25° C. to 45° C.

The cells may be harvested by centrifugation. The measurement of the rate of specific growth is made by measuring the increase in the dry weight of cells per unit of volume as a function of the time. The concentration of the methanol in the culture medium is measured by gas phase chromatography.

The strains obtained by the present method can be used not only for the synthesis of proteins from methanol, but also for the biological purification of an effluent from methanol, the possible reduction of methanol in fermented drinks, and, in general, in any fermentation involving methanol as a carbon substrate.

The following non-limiting examples are presented to illustrate practice of the present invention:

EXAMPLE 1

A strain identified as being of the genus *Pseudomonas stuzeri* is cultured on the following medium:

| Culture Medium ($M_1$) | |
|---|---|
| Ingredient | Amount |
| $NH_4Cl$ | 3 g. |
| $Na_2HPO_4$ | 3 g. |
| $KH_2PO_4$ | 0.5 g. |
| $CaCl_2$ | 0.01 g. |
| $FeSO_4$ | 0.001 g. |
| $ZnCl_2$ | 0.001 g. |
| $MnSO_4$ | 0.001 g. |
| $MgSO_4$ | 0.5 g. |
| $CH_3OH$ | 5 g. |
| Water Quantity Sufficient to Prepare | 1 liter |
| H is adjusted to 6.8 | |

The culture temperature is 30° C. and the generation time of this strain is 120 minutes. The apparent constant affinity for methanol (Ks) is determined to be 1090 ppm.

The effective production of biomass at the end of three days' culture is 0.30 grams per 1 gram of methanol.

A cellular suspension is harvested from this culture and is diluted in normal saline solution so as to produce about $10^8$ to $10^9$ cells per ml., before being spread on a medium ($M_1$) prepared with 2.5% by weight agar-agar and made up with 2% by weight glycine.

The petri dishes are placed in the oven at 30° C. The appearance of resistant mutants is manifested at the end of a few days. The colonies are sampled and seeded into liquid medium ($M_1$) in order to test their methylotrophic characters.

Several glycine-resistant mutants are obtained. The study of the kinetic performances of one of those mutants yielded the following results on the $M_1$ culture medium:

| Generation Time | 100 minutes |
|---|---|
| Ks Methanol | 20 ppm |

The effective production of biomass at the end of three days' culture is 0.40 g. per 1 g. of methanol.

EXAMPLE 2

Other mutants of the strain recovered in the procedure of Example 1 and resistant to 2% glycine were isolated with a preliminary treatment of the cellular suspension with 2% ethylmethane sulphonate for 2 hours at 30° C. at pH 7.4. The same improvements were found as in the mutant of Example 1, namely reduction in the generation time and above all great reduction of the Ks:

| (I) Wild Strain | | (II) Mutant Strain | |
|---|---|---|---|
| Generation Time | 120 minutes | Generation Time | 88 minutes |
| Ks Methanol | 1090 ppm | Ks Methanol | 20 ppm |

EXAMPLE 3

The treatment employed in the procedure of Example 1 is repeated using a strain of *Pseudomonas aeruginosa methylotrophus*. The mutants resistant to glycine are isolated on the selection sieve (medium $M_1$ + 0.5% glycine).

The kinetic performances of these new strains (on $M_1$ medium) are definitely improved compared to the wild strains, the results of which follow:

| (I) Wild Strain | | (II) Mutant Strain | |
|---|---|---|---|
| Generation | 5¾ Hours | Generation Time | 3½ Hours |
| Ks Methanol | 830 ppm | Ks Methanol | 100 ppm |

EXAMPLE 4

The treatment employed in the procedure of Example 1 is repeated using a strain of *Microccus varians methylotrophus*. It is, thus, possible to isolate strains exhibiting improved performances on methanol compared to the wild strain, the results of which follow:

| (I) Wild Strain | | (II) Mutant Strain | |
|---|---|---|---|
| Generation | 4½ Hours | Generation Time | 3½ Hours |
| Ks Methanol | 450 ppm | Ks Methanol | 150 ppm |

Inasmuch as many changes and variations in detail are possible and which are readily apparent to those skilled in the art within the scope of the present invention, it is intended that the description thereof is illustrative rather than limiting.

What is claimed is:

1. A method for synthesizing proteins from methanol which comprises
   (a) culturing a *Psuedomonas stuzeri*, *Pseudomonas aeruginosa methylotrophus*, or a *Micrococcus varians methylotrophus* micro-organism on a medium containing methanol as the sole carbon source and glycine at a sufficient temperature, and pH, to produce glycine resistant methylotrophic mutant strains, (b) recovering said mutant strains, and (c) culturing said mutant strains at a sufficient temperature and pH to produce proteins.

2. The method of claim 1, wherein the concentration of glycine in the medium is between about 0.5 to 2% by weight.

3. The method of claim 1, wherein the concentration of methanol in the medium is between about 0.5 to 2% by weight.

4. The method of claim 1, wherein the medium contains mineral salts and nitrogen in mineral form.

5. The method of claim 1, wherein the culturing is carried out at a temperature of 25° C. to 45° C.

* * * * *